United States Patent
Theodoropulos

(10) Patent No.: US 6,605,740 B2
(45) Date of Patent: Aug. 12, 2003

(54) FLUORESCENT DYES FOR THE LABELING OF BIOLOGICAL SUBSTRATES

(76) Inventor: Spyros Theodoropulos, 2964 Hickory St., Yorktown Heights, NY (US) 10598

( * ) Notice: Subject to any disclaimer, the term of this patent is extended or adjusted under 35 U.S.C. 154(b) by 289 days.

(21) Appl. No.: 09/823,092

(22) Filed: Apr. 2, 2001

(65) Prior Publication Data

US 2002/0147354 A1 Oct. 10, 2002

(51) Int. Cl.⁷ .............................................. C07C 249/00
(52) U.S. Cl. .......................................... 562/41; 562/440
(58) Field of Search ................................... 562/41, 440

(56) References Cited

FOREIGN PATENT DOCUMENTS

| JP | 137154 | * | 6/1986 |
| JP | 051185 | * | 3/1988 |
| JP | 244361 | * | 9/1989 |

OTHER PUBLICATIONS

Bigelow, R.W et al , Journal of Electron Spectroscopy and Related Phenomena (1988) 46(1) 1–17.*

* cited by examiner

Primary Examiner—Paul J. Killos
(74) Attorney, Agent, or Firm—William R. Moran

(57) ABSTRACT

This invention provides a new class of squaraine dyes having moieties which serve for the covalent attachment to biological substrates and resulting in the fluorescent labeling of the substrates. The labeled substrates are intended for use in analytical techniques for the detection and measurement of biological and clinical compounds of interest.

7 Claims, No Drawings

FLUORESCENT DYES FOR THE LABELING OF BIOLOGICAL SUBSTRATES

BACKGROUND OF THE INVENTION

1) Field of the Invention

Functionalized dyes bearing moieties for the attachment to biological substrates are very important, serving in the detection of disease in biological fluids and the detection of a variety of analytes such as environmental contaminants and toxins in food.

This invention relates to a new class of squaraine dyes which are equipped with functionalities serving in the covalent attachment of these dyes to biological substrates forming conjugates resulting in the fluorescent labeling of the substrate.

The novel compounds are intended for use in analytical techniques for the detection and measurement of biological and clinical compounds of interest. Typical examples of such compounds are bacteria, viruses, enzymes, hormones, antibodies, proteins, derivatized oxy and deoxy polynucleic acids, drugs and other materials.

2) Description of the Prior Art

Squaraine dyes are known in the art as compounds derived by reaction of squaric acid and aromatic nucleophiles. Structural and physical chemical characteristics of squaraine dyes are described by Sprenger, et al in Angew chem. 80, 541 (1968). The type of squaraine dyes thereof having the aromatic nucleus directly attached to the squaric moiety have been known for quite some time and their use as photosensitizers, photoconductive devices and in the labeling of red blood cells has been reported. None of these dyes however has been covalently coupled to biological substrates nor have any of these dyes been, in actuality, made with functional groups which allow for the covalent coupling to substrates of interest. Accordingly, it is an object of the present invention to provide novel derivatives of squaraine dyes which may be readily coupled to compounds of clinical or biological interest to provide conjugates which exhibit intense fluorescence. A further object of the invention lies in the coupling of the novel dyes to form adducts with a broad spectre of biological and clinical compounds by facile and gentle chemical reactions. Other objects and advantages of the present invention will become apparent from the following detailed description of the invention.

While the invention is susceptible to various modifications and alternative forms, there will herein be described in detail the preferred embodiments. It is not intended to limit the invention to the specific forms disclosed. On the contrary, it is intended to cover all modifications and alternative forms falling within the spirit and scope of the invention as expressed in the appended claims.

SUMMARY OF THE INVENTION

The present invention is directed to novel derivatives of squaraine dyes which contain moieties which allow for the covalent coupling of these dyes to a variety of biological substrates and other organic molecules. The resulting conjugates provide intense fluorescent haptens, antigens, drugs, antibodies, peptides, enzymes, oxy and deoxy polynucleic acids which can be used in the development of fluorescent analytical techniques. The basic structure of the functionalized squaraine dyes is structurally represented by the formula I.

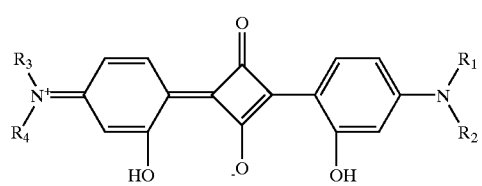

I wherein $R_1$ is a lower carboxyalkyl (1–7 carbon atoms); $R_2$ is hydrogen, a lower alkyl group (1–7 carbon atoms); a lower alkyl 1–7 carbon atoms and which may be substituted with groups selected from —$SO_3H$, —$PO_3H_2$, —COOH and —$NHSO_3H$; $R_3$ is a lower alkyl (1–5 carbon atoms), lower carboxyalkyl (1–7 carbon atoms) or a lower alkyl group 1–7 carbon atoms containing substituents selected from the group consisting of —$SO_3H$, —$PO_3H_2$, —COOH; and —$NHSO_3H$); $R_4$ is hydrogen, (alkyl 1–5 carbon atoms, or lower alkyl 1–7 carbon atoms which may be substituted with groups selected from —$SO_3H$, —$PO_3H_2$, —COOH and —$NHSO_3H$).

Two examples representing I by structural formula are shown in II and III:

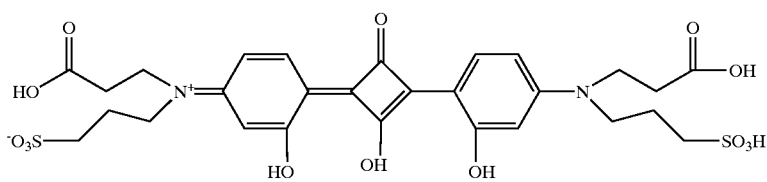

II

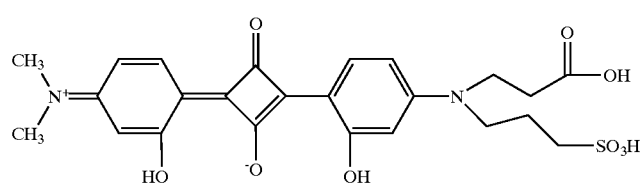

III

DETAILED DESCRIPTION OF THE INVENTION

The squaraine dyes of the invention represented structurally in I

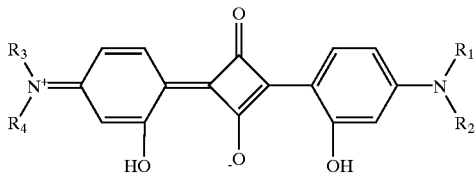

I wherein $R_1$ is a lower carboxyalkyl (1–7 carbon atoms), $R_2$ is hydrogen, an alkyl group (1–7 carbon atoms), a lower alkyl group (1–7 carbon atoms) which may be substituted with groups selected from —$SO_3H$, —$PO_3H_2$, —COOH and —$NHSO_3H$; $R_3$ is a lower alkyl (1–5 carbon atoms), a lower carboxyalkyl (1–7 carbon atoms) or a lower alkyl group (1–7 carbon atoms) containing substituents selected from the group consisting of —$SO_3H$, —$PO_3H_2$ and —$NHSO_3H$; $R_4$ is hydrogen, alkyl (1–5 carbon atoms) or a lower alkyl (1–7 carbon atoms) which may be substituted with groups selected from —$SO_3H$, —$PO_3H_2$, COOH and —$NHSO_3H$;

are ideal fluorescent agents due to their attractive fluorescent emissions exhibited at wavelengths above 580 nanometers. The carboxyalkyl group in the $R_1$ or $R_3$ moieties provide an active hydrogen bonding site and functions most suitably to promote coupling of the dye with organic substrates of interest.

The squaraine dyes of the invention were synthesized using known techniques. The symmetrical dyes, where $R_1$ and $R_2$ are the same as $R_3$ and $R_4$, were prepared by reacting the aromatic nucleophiles with squaric acid in the presence of a polar aprotic solvent and a conventional solvent. A one to one mixture of n-butanol and benzene or toluene, is the solvent system previously applied, although a solvent such as methanol or ethanol can be used as well. For the preparations of the unsymmetrical squaraine dyes where $R_1$ and $R_2$ are different from $R_3$ and $R_4$, the method described by Joseph R. Lukowicz in "Dyes and Pigments" 21(1993), 227–234, was applied. Details of this method utilizing two different aromatic nucleophiles and 3,4-diethoxy-cyclobutanedione will become apparent in the experimental section.

The squaraine dyes of the invention may be reacted with any compound of interest capable, of course, of reacting with the carboxyalkyl group. For example, any compound containing (in the classical sense) an active hydrogen group may be coupled to the carboxyalkyl of the squaraine dyes, e.g. any compound containing a hydroxyl or an amino group with active hydrogen can be utilized. Accordingly, a wide number of amino acids, peptides, proteins, enzymes, drugs, pesticides, derivatized oxy and deoxy polynucleotides and nucleotides, various natural products, plant and animal hormones, polyamines, viruses, bacterial cells and other metabolites contain groups reactive with the carboxylic group can be employed.

The squaraine dyes of the invention can be covalently bound to organic substrates through the carboxyalkyl group by utilizing known process conditions. It is suitable to activate the dye containing the carboxylic group with a carbodiimide, e.g. cyclohexyl carbodiimide or the water soluble carbodiimide known in the art as EDC, in a polar solvent such as dimethylformamide, dimethylsulfoxide or in aqueous buffers. After the activation, the solution containing the dye is added to the solution containing the substrate. Proteinecious substrates are usually dissolved in aqueous buffered solutions, non-proteinecious substrates can be dissolved in a variety of solvents which are inert to the reaction partners such as dimethylformamide, dimethylsulfoxide, pyridine and other solvents including aqueous buffered solutions. Another method adapted in the coupling of carboxylic moieties to organic molecules containing active hydrogen groups is utilizing a succinimide activated ester of the carboxylic group. The succinimidyl ester of carboxylic-containing molecules can be prepared and isolated prior to coupling to the substrates, or made in situ and used in further couplings without isolation.

Thus, in accordance with the present invention, conjugates of carboxylic derivatives of squaraine dyes and organic substrates can be illustrated by the following formula:

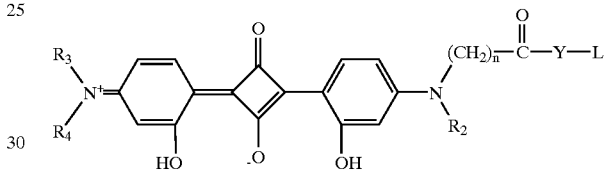

wherein n=1–6; $R_2$, $R_3$ and $R_4$ are the same as defined above; Y is oxygen, primary or secondary amino group; and L is an organic substrate containing a functional group consisting of amino or hydroxyl.

The coupling of the dyes was carried out in a variety of solvents depending on the nature of the amine-substrate or the hydroxyl-substrate. The coupling of proteins was carried out in a variety of buffers, such as carbonates, phosphates or MES using the carbodiimide technique or the succinate ester. The PH of the reaction ranged from 1–12, but a PH of 5–10 was preferred. The reaction time and temperature was appropriately selected depending on the stability and nature of the protein. The preferred reaction time was 1 to 24 hours and the preferred temperature was 4° C. to ambient. The coupling to oligonucleotides was carried out in carbonate or phosphate buffers PH-8 or directly in pyridine-DMF solvent mixture with the succinimidyl ester of the dye made in situ in DMF solution. Details of these and couplings to other substrates will become apparent in the experimental section of this invention.

Conjugates of carboxyalkyl derivatives of squaraine dyes with organic substrates of interest are intended for use in many of the several known techniques involving fluorescent tagging or fluorescent competitive binding to detect and measure a compound or analyte of interest. The particular conjugates used will be dependent upon the type of tagging required by the technique of choice and the technique selected will be determined by the results as required. The squaraine conjugates of this invention are particularly advantageous since they exhibit little deleterious effects on the biological compounds and emit at wavelengths which are above 580 nanometers.

Specific examples of compounds represented by formula I are:

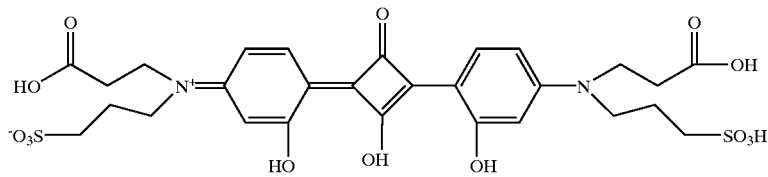

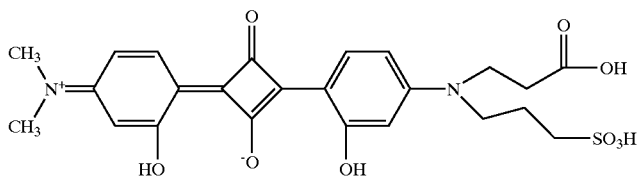

EXAMPLE 1

3-[(N-carboxyethyl-N-Sulfopropyl)amino]phenol

A mixture of 3-[(N-carboxyethyl)amino]phenol, 1.48 grams and propane sulfone 2.5 g (excess) were mixed and heated in an oil bath at 125° C. for twenty minutes. The mixture dissolved in methanol and the product purified by silica gel column chromatography. The column eluted with ethyl acetate to remove bi-products and then with methanol to elute the product.

EXAMPLE 2

Preparation of II

1-[4-(N-carboxyethyl-N-Sulfopropyl)immonio-2-Hydroxyl-2,5-Cyclo-Hexadienylidene]-3-[4-(N-Carboxyethyl-N-Sulfopropyl)amino-2-Hydroxy]phenyl-2-oxo-4-Hydroxyl-3-Cyclobutene.

structure:

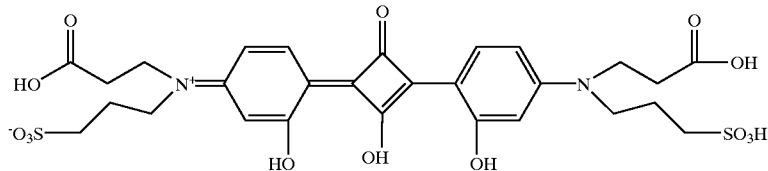

Squaric acid 116 mg and 600 mg of 3-[(N-Carboxyethyl-N-Sulfopropyl)amino]-phenol were mixed in 10 ml of toluene and 10 ml of n-butanol in a flask and heated to reflux under an argon atmosphere with azeotropic removal of water overnight. Allowed to cool to room temperature and the product purified by silica-gel column chromatography. The solvents used to elute the column were ethyl acetate and methanol. The blue band containing the product was eluted at the end with methanol. The product characterized by ultraviolet absorption showed:

U.V. max (methanol) 641 nm.

EXAMPLE 3

Attachment of II to Oligonucleotides

In an Eppendorf tube was placed 2 mg of the dye of Example 1 and dissolved with 200 ml of pyridine. To this were added 2.0 mg of dicyclohexycarbodiimide and 3 mg of N-hydroxysuccinimide (NHS). The mixture was stirred at ambient temperature for two days. The reaction was centrifuged and the supernatan was added in an Eppendorf tube of ≈1.5 O.D. containing 2 ml of 18 base aminohexyl derivatized oligonucleotide obtained from LTI and dried using a speed-vac evaporator. Incubated for 5 hours, after which pyridine was removed by lyophilization. The conjugate was purified on high-pressure liquid chromatography using c-18 reverse-phase column and linear gradient of 1% TFA in water and 1% TFA in acetonitrile over a period of 30 minutes starting at 100% of 1% TFA/H2O and going to 1% TFA/AcN. The conjugate eluted at 3–4 minutes under these conditions.

EXAMPLE 4

Attachment of II to Protein 2 mg of the dye II made according to Example 1 was dissolved in 200 microliters of DMF. To this was added 2.0 mg of dicyclohexylcarbodiimide (DCC) followed by 3.0 mg of N-hydroxysuccinimide and the reaction stirred at ambient temperature for 4 days.

The DMF solution containing the succinate ester of the dye was added without purification into 1.0 mg of human-1

Gg dissolved in 0.5 ml of sodium bicarbonate buffer PH-8 and stirred gently for five hours. The conjugate was purified on G-50 sephardex column using the same buffer. The labeled protein showed an excitation at 638 nm and an emission at 665 nm.

What is claimed:

1. A squaraine dye of the formula:

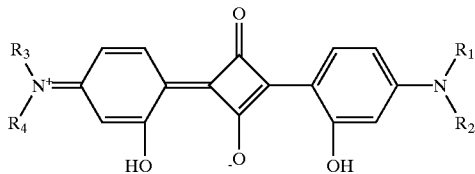

wherein $R_1$ is a lower carboxyalkyl of 1–7 carbon atoms;

$R_2$ is hydrogen, lower alkyl of 1–7 carbon atoms, lower alkyl of 1–7 carbon atoms which may be substituted with groups selected from the group consisting of —$SO_3H$, $PO_3H_2$, —COOH and —$NHSO_3H$;

$R_3$ is a lower alkyl of 1–5 carbon atoms, lower carboxy alkyl of 1–7 carbon atoms, lower alkyl 1–7 carbon atoms containing substituents selected from the group consisting of —$SO_3H$, $PO_3H_2$, —COOH and —$NHSO_3H$;

$R_4$ is hydrogen, alkyl of 1–5 carbon atoms or lower alkyl of 1–7 carbon atoms which may be substituted with groups selected from the group consisting of —$SO_3H$, $PO_3H_2$, —COOH and —$NHSO_3H$.

2. A squaraine dye of the formula:

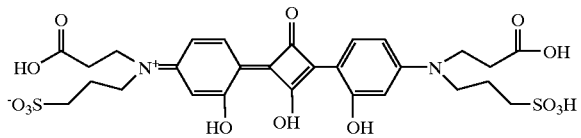

3. A squaraine dye of the formula:

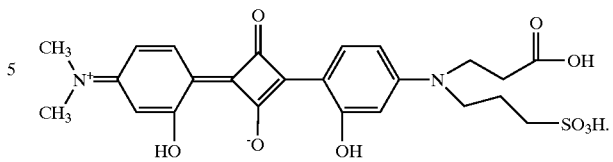

4. A squaraine dye conjugate of the formula:

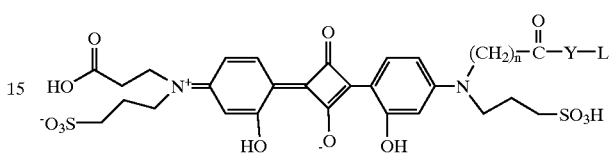

wherein N is 1 to 6;

Y is oxyen, primary, secondary or tertiary amino group; and

L is an organic substrate containing a functional group consisting of amino or hydroxyl.

5. A squaraine dye conjugate of the formula:

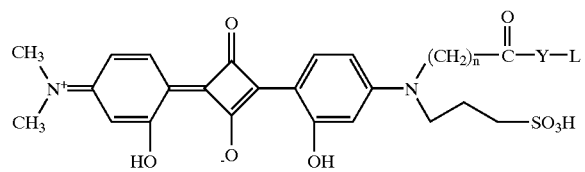

wherein n=1 to 6; and

Y and L are the same as claimed in claim 4.

6. A squaraine dye conjugate of the formula of claim 4 wherein n=2.

7. A squaraine dye conjugate of the formula of claim 5 wherein n=2.

* * * * *